(12) United States Patent
Hoffman et al.

(10) Patent No.: US 9,026,531 B2
(45) Date of Patent: May 5, 2015

(54) ASSOCIATING MULTIPLE DATA SOURCES INTO A WEB-ACCESSIBLE FRAMEWORK

(75) Inventors: Mark A. Hoffman, Lee's Summit, MO (US); Kevin M. Power, Kansas City, MO (US); Kathleen M. Gorman, Los Angeles, CA (US); Aaron Bush, Kearney, MO (US); Michelle Siefert, Kansas City, MO (US); Matthew F. Emons, West Hollywood, CA (US)

(73) Assignee: Cerner Innovation, Inc., Kansas City, KS (US)

( * ) Notice: Subject to any disclaimer, the term of this patent is extended or adjusted under 35 U.S.C. 154(b) by 51 days.

(21) Appl. No.: 13/449,024

(22) Filed: Apr. 17, 2012

(65) Prior Publication Data

US 2013/0275361 A1    Oct. 17, 2013

(51) Int. Cl.
*G06F 17/30* (2006.01)
*G06F 19/00* (2011.01)

(52) U.S. Cl.
CPC ...... *G06F 19/3456* (2013.01); *G06F 17/30899* (2013.01); *G06F 17/3089* (2013.01); *G06F 19/3493* (2013.01)

(58) Field of Classification Search
USPC .......................... 707/602, 999.102, 736, 803
See application file for complete search history.

(56) References Cited

U.S. PATENT DOCUMENTS

| | | | | |
|---|---|---|---|---|
| 6,191,117 B1 * | 2/2001 | Kozachuk | | 514/23 |
| 8,032,398 B1 * | 10/2011 | Kelly et al. | | 705/3 |
| 8,443,089 B2 * | 5/2013 | Mosleh et al. | | 709/227 |
| 2002/0032582 A1 * | 3/2002 | Feeney et al. | | 705/2 |
| 2003/0187688 A1 * | 10/2003 | Fey et al. | | 705/2 |
| 2003/0216943 A1 * | 11/2003 | McPhee et al. | | 705/3 |
| 2004/0122706 A1 * | 6/2004 | Walker et al. | | 705/2 |
| 2004/0189718 A1 * | 9/2004 | Stein et al. | | 345/853 |
| 2007/0092440 A1 * | 4/2007 | Braendle | | 424/1.11 |
| 2007/0156344 A1 * | 7/2007 | Sender et al. | | 702/19 |
| 2007/0255585 A1 * | 11/2007 | Moussavi et al. | | 705/2 |
| 2008/0133273 A1 * | 6/2008 | Marshall | | 705/3 |
| 2009/0172773 A1 * | 7/2009 | Moore | | 726/1 |
| 2009/0313048 A1 * | 12/2009 | Kahn et al. | | 705/3 |
| 2010/0011302 A1 * | 1/2010 | Stein et al. | | 715/753 |
| 2011/0022025 A1 * | 1/2011 | Savoie et al. | | 604/500 |
| 2012/0029932 A1 * | 2/2012 | Stein et al. | | 705/2 |
| 2012/0072232 A1 * | 3/2012 | Frankham et al. | | 705/2 |

(Continued)

OTHER PUBLICATIONS

Wang, "Birth Weights Fell From 1990 to 2005," Wall Street Journal, Jan. 22, 2010. Retrieved on Aug. 15, 2013 from http://online.wsj.com/article/SB10001424052748704423204575017471267586344.html.*

(Continued)

*Primary Examiner* — Cam-Linh Nguyen
(74) *Attorney, Agent, or Firm* — Shook Hardy & Bacon LLP

(57) ABSTRACT

Systems, methods, and computer-readable media for associating multiple data sources into a web-accessible framework. Health data is received from multiple data sources and is used to populate a framework comprising at least one topic focused data mart. Each topic focused data mart has a common structure and is associated with a web service providing standard features supported by each topic focused data mart and custom features specific to a topic associated with each topic focused data mart. In various embodiments, demographic information is received from a clinician and is utilized to present context-specific data derived from the topic focused data mart.

20 Claims, 3 Drawing Sheets

(56) References Cited

U.S. PATENT DOCUMENTS

| | | | |
|---|---|---|---|
| 2012/0101849 A1* | 4/2012 | Mathur et al. | 705/3 |
| 2012/0128702 A1* | 5/2012 | Weinschenk et al. | 424/184.1 |
| 2012/0173285 A1* | 7/2012 | Muthukrishnan | 705/3 |
| 2013/0002847 A1* | 1/2013 | Zahniser et al. | 348/79 |

OTHER PUBLICATIONS

Stafford, "A Curve That Fits Canadian Provincial Birthweights," Canadian Studies in Population, vol. 4, 1977, p. 33. Retrieved on Aug. 16, 2013 from http://ejournals.library.ualberta.ca/index.php/csp/article/download/16081/12886.*

* cited by examiner

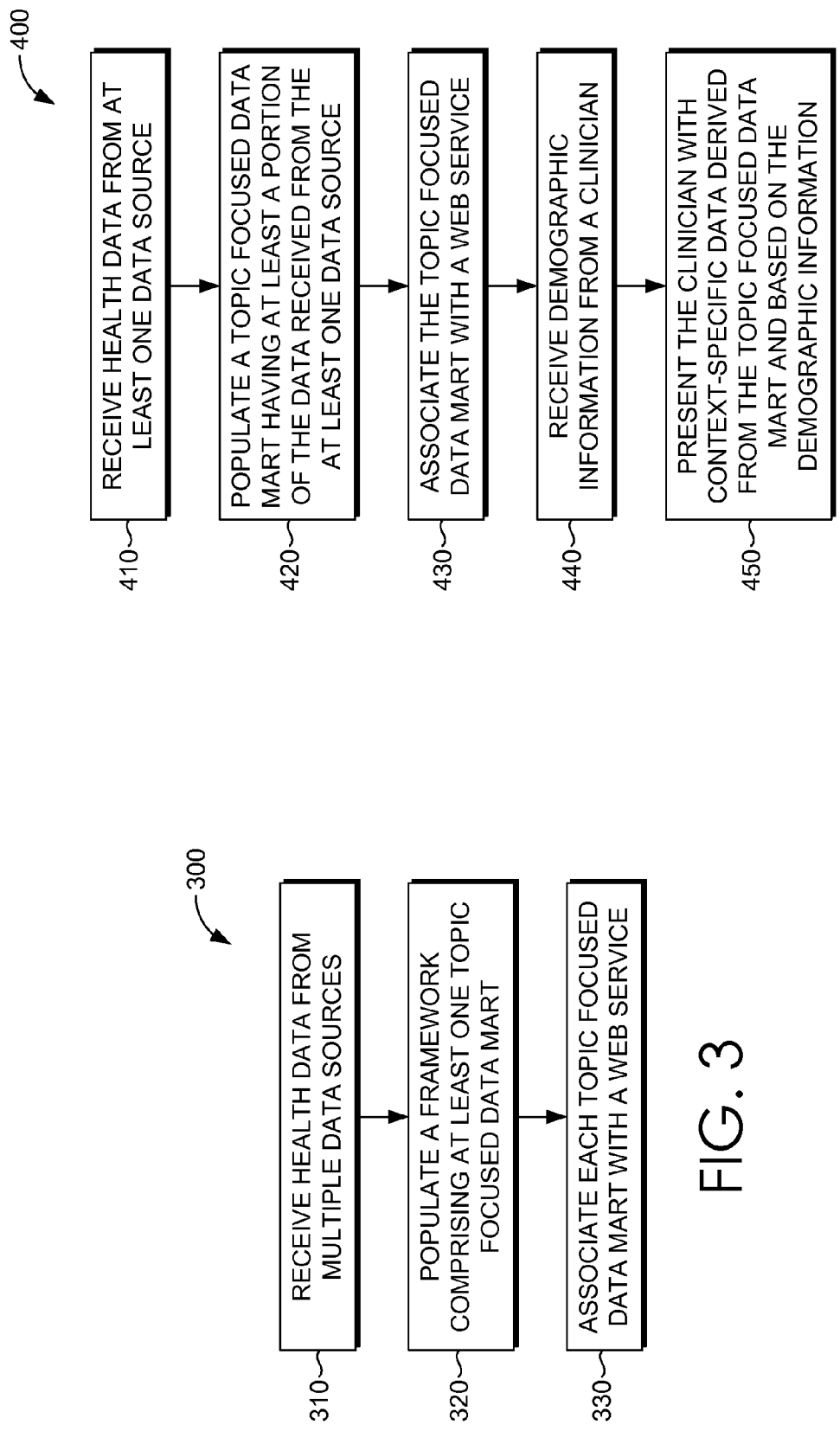

ASSOCIATING MULTIPLE DATA SOURCES INTO A WEB-ACCESSIBLE FRAMEWORK

BACKGROUND

The advent of powerful servers, large-scale data storage and other information infrastructure has spurred the development of advanced data warehousing and data mining applications. Structured query language (SQL) engines, on-line analytical processing (OLAP) databases and inexpensive large disk arrays have, for instance, been harnessed in financial, scientific, medical, and other fields to capture and analyze vast streams of transactional, experimental, and other data. The mining of that data can reveal sales trends, weather patterns, disease epidemiology and other patterns not evident from more limited or smaller-scale analysis.

In the case of health-related data management, the task of receiving, conditioning, and analyzing large quantities of clinical information in real-time is particularly challenging. The sources of health-related data for an organization to better provide context, for instance, include large data warehouses, such as statehealthfacts.org, data.gov, and clinical trials.gov, each of which may store many terabytes of data. The variety and depth of data represented in these data warehouses impedes the performance of typical querying strategies. Although there is widespread belief that data in these data warehouses can be used to inform health care and health at the personal and institutional levels, they are not structured to support real-time web access or implemented in a manner sufficiently robust to support health care delivery.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to systems, methods, and computer-readable media for, among other things, associating multiple data sources into a web-accessible framework. In one embodiment, computer storage media having computer-executable instructions embodied thereon, that when executed, perform a method for associating multiple data sources into a web-accessible framework. Health data is received from multiple data sources. A framework comprising at least one topic focused data mart is populated. Each topic focused data mart receives at least a portion of the data from the multiple data sources and each topic focused data mart has a common structure. Each topic focused data mart is associated with a web service providing standard features supported by each topic focused data mart and custom features specific to a topic associated with each topic focused data mart.

In another embodiment of the present invention, computer storage media having computer-executable instructions embodied thereon, that when executed, perform a method for presenting context-specific data derived from one or more web-accessible, topic focused data marts. Health data is received from at least one data source. A topic focused data mart is populated with at least a portion of data received from the at least one data source. The topic focused data mart is associated with a web service. Demographic information is received from a clinician. The clinician is presented with context-specific data derived from the topic focused data mart and based on the demographic information.

In yet another embodiment of the present invention, a computer system for associating multiple data sources into a framework comprises a processor couple to a computer storage medium, the computer storage medium having stored thereon a plurality of computer software components executable by the processor. A health data component receives health data from multiple sources. A framework component populates a framework comprising at least one topic focused data mart, each topic focused data mart having at least a portion of the data received from the multiple data sources and each topic focused data mart having a common structure. A web service component associates each topic focused data mart with a web service providing standard features supported by each topic focused data mart and custom features specific to a topic associated with each topic focused data mart. A listener component provides a listener for updating at least a portion of the health data. A request component receives a request for at least a portion of the health data. A connection component enables connection points to an Electronic Health Record (EHR), a Public Health Record (PHR), or an administrative dashboard. A demographic component receives demographic information from a clinician. A presentation component presents the clinician with context-specific data derived from one or more topic focused data marts and based on the demographic information.

BRIEF DESCRIPTION OF THE DRAWINGS

The present invention is described in detail below with reference to the attached drawings figures, wherein:

FIG. 3 is a flow diagram showing a method for associating multiple data sources into a framework, in accordance with an embodiment of the present invention; and FIG. 4 is a flow diagram showing a method for presenting context-specific data derived from one or more web-accessible, topic focused data marts, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention can empower a patient's, clinician's, or organization's ability to harness pertinent data across multiple data warehouses to access, in real-time, topic focused data marts efficiently and with limited knowledge of the underlying data structure. Embodiments present advantages over other systems which are limited to querying data from static, or outdated, content by associating each topic focused data mart with a web service.

A topic focused data mart refers to a subset of data from one or more data warehouses, typically oriented to a specific purpose or major data subject. Topic focused data marts are analytical data stores designed to focus on a specific community or purpose within an organization. Topic focused data marts are often derived from subsets of data in various data warehouses.

Therapeutic drug monitoring (TDM) refers to testing of medication levels to determine whether a patient is receiving an optimal dosage of the medication. Because there is complex interaction between patient characteristics and drug properties, the rate at which medications accumulate in the body varies considerably. TDM is a type of pharmacokinetic assessment to determine concentration of medication in patients' bodies through laboratory tests, particularly serum blood levels. For example, drug metabolism is influenced by factors such as weight, kidney/liver functioning, drug half-life, repeated doses, and routes of administration. Although standard dosage recommendations exist, clinicians often adjust and individualize treatment.

Figure 1:
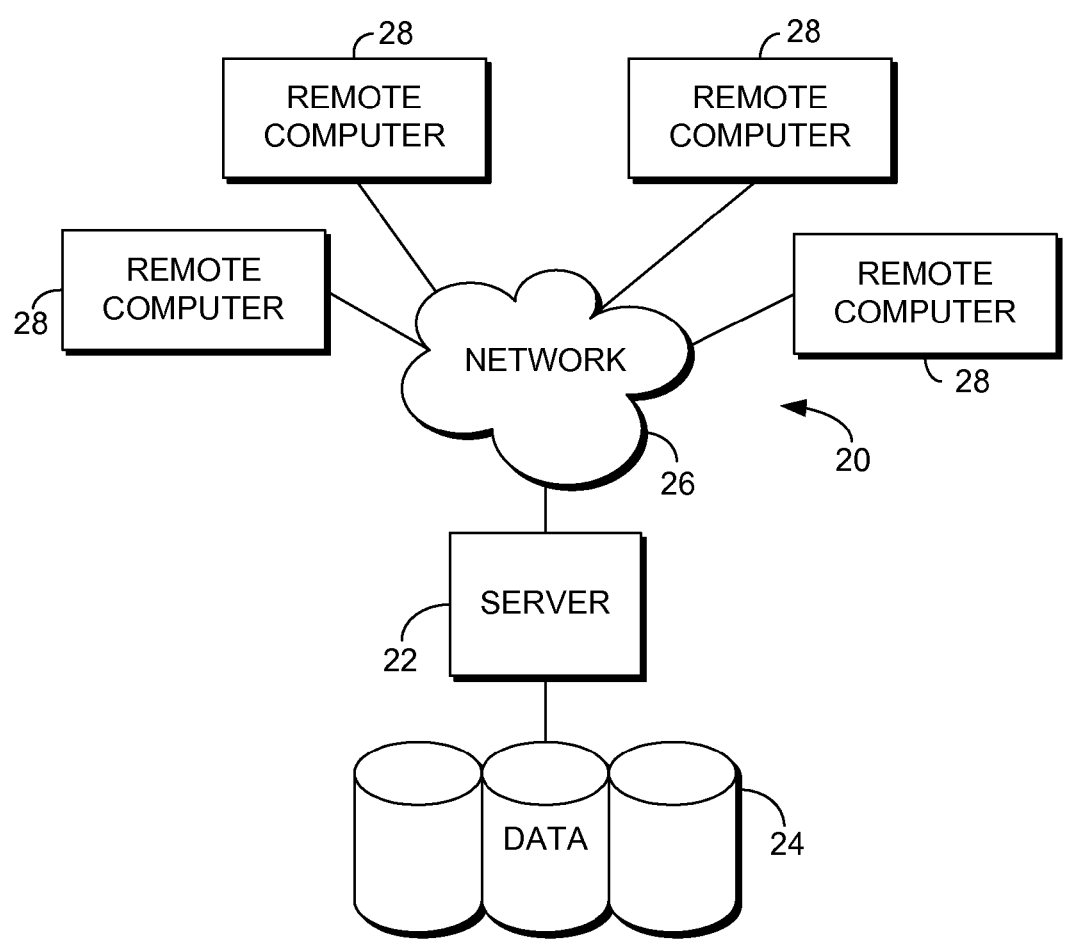
FIG. 1 is a block diagram of an exemplary computing system suitable for use in implementing embodiments of the present invention.

Having briefly described embodiments of the present invention, an exemplary operating environment suitable for use in implementing embodiments of the present invention is described below. Referring to FIG. 1 an exemplary computing environment with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, mini-computers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary computing environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

Figure 2:
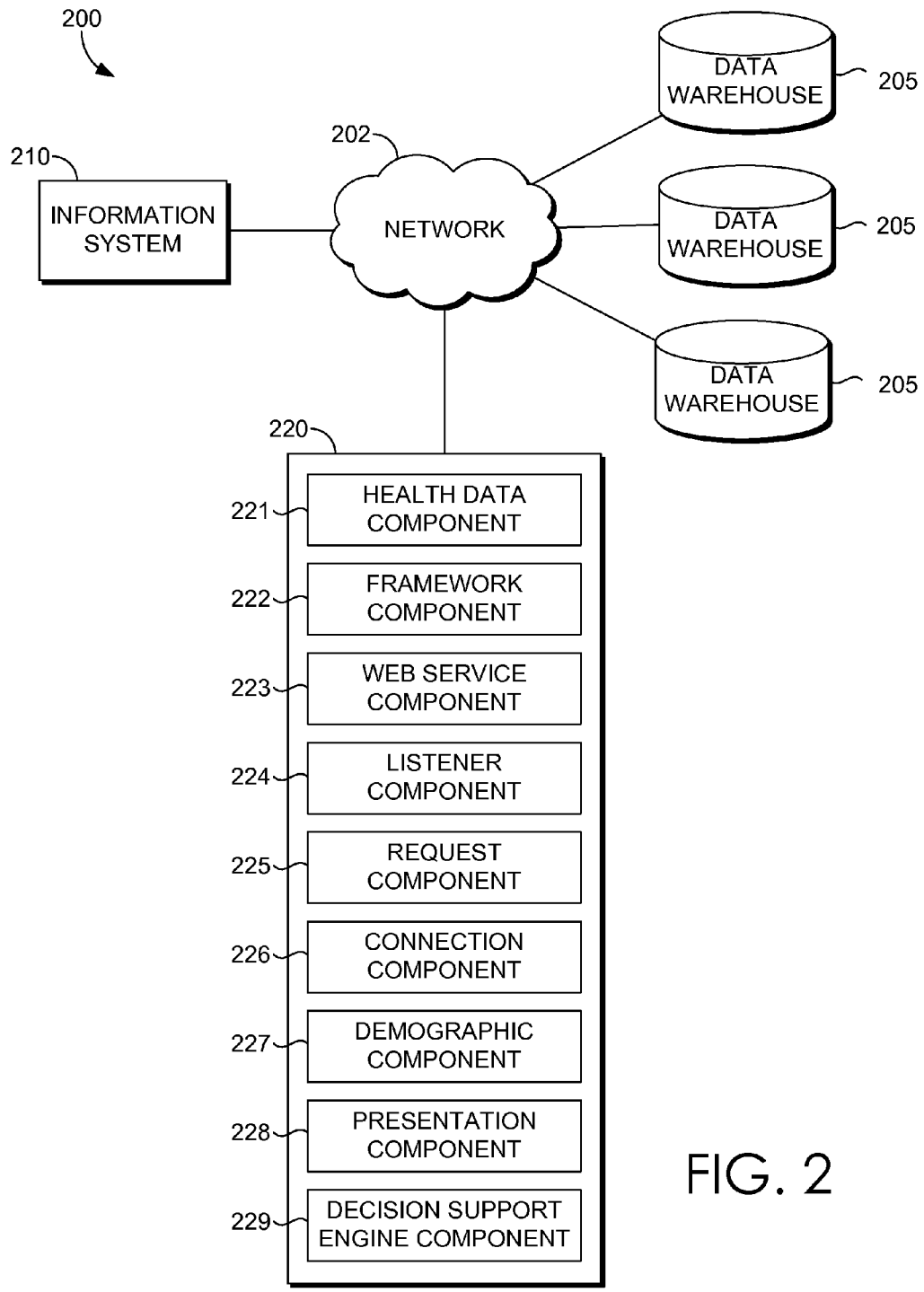
FIG. 2 schematically shows a network environment suitable for performing embodiments of the invention.

Referring now to FIG. 2, a block diagram is provided illustrating an exemplary system 200 in which a framework engine 220 is shown interfaced with an information system 210 in accordance with an embodiment of the present invention. The information system 210 may be a comprehensive computing system within a clinical environment similar to the exemplary computing system 20 discussed above with reference to FIG. 1.

The information system 210 may be connected via the network to one or more data warehouses 205, storing various forms of data collected by third parties such as statehealthfacts.org, data.gov, and clinical trials.gov. The data warehouses store data collected from a variety of sources and comprising many data elements. An internal data warehouse may be utilized by information system 210 and may be stored within the information system 210 or external to the information system 210.

The framework engine 220 is generally configured to associate multiple data sources into a framework, reducing the work effort required to implement application programming interfaces (APIs) for each topic specific data mart. Each topic specific data mart is associated with a web service which provides standard features supported for all topic specific data marts. These standard features include security and request/reply interactions. Features specific to the topic of the node are also provided. The topic specific data marts are accessible via standard web services calls, thereby enabling a wide variety of connection points to the EHR, PHR, or administrative dashboard. The ability to evaluate benchmarks across data sources is also enhanced by utilizing web services calls.

In some embodiments, the data is a blend of proprietary and publically available data to better provide context for a patient seeking health care or a person seeking to improve their health. In other embodiments, the data supports administrative and patient specific scenarios using a common framework. In one embodiment, a web services layer allows the front end implementation to be separate from the back end data layer, promoting reuse of the service for multiple venues.

As shown in FIG. 2, the framework engine 220 includes health data component 221, framework component 222, web service component 223, listener component 224, request component 225, connection component 226, demographic component 227, and presentation component 228. In one embodiment, the framework engine 220 also includes decision support engine component 229.

Health data component 221 receives health data from multiple sources. In various embodiments, the health data is public health data including average birth weights, a list of clinical trials, comparison metrics such as length of stay by condition, TDM levels, and air quality results. In one embodiment, the health data is internal data collected by a health care facility or institution. In other embodiments, the health data is stored in large publically available data warehouses, such as statehealthfacts.org, data.gov, and clinical trials.gov. In other embodiments, the health data is stored in proprietary data warehouses. In one embodiment, health data component 221 derives new data from the health data. For example, health data component 221 may receive discrete health data and summarize it at various time levels (e.g., by day, week, month, etc.).

Framework component 222 populates a framework comprising at least one topic focused data mart. Each topic focused data mart comprises at least a portion of the data received from the multiple data sources. Because each topic focused data mart represents a subset of the data that is available, the topic focused data marts can be queried much more efficiently than a larger data warehouse. Each topic focused data mart also has a common structure allowing disparate data to be accessed by similar front-end methods. Such a common structure also facilitates a real-time web access that allows the front end implementation to be separated from the back end data layer and promotes reuse by multiple venues. Each topic focused data mart, in one embodiment, is accessible via the network similarly to the data warehouses 205. In this embodiment, the framework component 222 populates the framework via the network. In another embodiment, each topic focused data mart is stored within the framework engine 220.

Web service component 223 associates each topic focused data mart with a web service. The web service provides standard features supported by each topic focused data mart. Such standard features may include security and request/reply interactions. In addition, the web service provides custom features specific to a topic associated with each topic focused data mart. The use of web services calls to access each topic focused data mart further enables a wide variety of connection points to the EHR or PHR, including administrative dashboards or any applications designed to support a variety of calls.

Listener component 224 provides a listener for updating at least a portion of the health data. The listener allows each topic focused data mart to maintain current data. Querying the larger, public data warehouse would require significant overhead and is not a practical solution for support real-time access. However, because each topic focused data mart is streamlined with data relevant to the given topic, the listener enables each topic focused data mart to maintain up-to date data while also supporting real-time access.

Request component 225 receives a request for at least a portion of the health data. For example, a clinician may be treating a patient taking certain medications. The clinician may want to verify the patient is receiving an optimal dosage of the medication. Laboratory results are compared with health data related to the medication that indicate whether the patient is receiving a dosage that is likely to be effective and not have an increased risk of adverse events.

Connection component 226 enables, in various embodiments, connection points to an EHR, PHR, administrative dashboard, or any application that can communicate with a web service. The connection points allow the EHR or PHR, in one embodiment, to communicate with the web service to transmit demographic information and receive context-specific data from a topic focused data mart. In one embodiment, an EMR associated with a patient is automatically populated with the context-specific data. This allows a clinician treating a patient to view information associated with the health data that is relevant to the patient, without requiring the clinician to query the topic focused data mart or enter any demographic information. Rather, the demographic information is pulled from the EMR and is used to query the topic focused data mart and the context-specific data is automatically received by and presented in the EMR.

Demographic component 227 receives demographic information from a clinician. In one embodiment, the demographic information is automatically received from the EHR associated with a patient. The demographic information may include geographical information, institution information, information related to characteristics of the patient, and the like.

Presentation component 228 presents the clinician with context-specific data derived from one or more topic focused data marts and the demographic information. In one embodiment, the context-specific data is average birth weights for the county, state, and/or country. In one embodiment, the context-specific data is a list of clinical trials for which a patient is eligible. In one embodiment, the context-specific data is length of stay by condition. In one embodiment, the context-specific data is TDM levels in serum across institutions. In one embodiment, the context-specific data is environmental information. In one embodiment, the context-specific data is epidemic information.

Decision support engine component 229, in one embodiment, enables a decision support engine to send alerts associated with the context-specific data. For example, a topic focused data mart may summarize air quality results from public sources in a region. The decision support engine receives this information along with the demographic information and sends alerts to potentially affected asthma patients.

With reference to FIG. 3, an exemplary flow diagram representative of a method for associating multiple data sources into a framework, in accordance with an embodiment of the present invention is shown and referenced generally by numeral 300. Method 300 may be implemented using the above-described exemplary computing system environment (FIG. 1). Initially, as shown at step 310, health data is received from multiple data sources. As described above, in various embodiments, the health data is average birth weights, a list of clinical trials, comparison metrics such as length of stay by condition, TDM levels, and air quality results. In one embodiment, the health data is internal data collected by a health care facility or institution. In other embodiments, the health data is stored in large publically available data warehouses, such as statehealthfacts.org, data.gov, and clinical trials.gov. In other embodiments, the health data is stored in proprietary data warehouses.

At step 320, a framework comprising at least one topic focused data mart is populated. Each topic focused data mart comprises at least a portion of the data received from the multiple data sources. Each topic focused data mart also has a common structure. As noted above, such a common structure facilitates a real-time web access that allows the front end implementation to be separated from the back end data layer and promotes reuse by multiple venues.

At step 330, each topic focused data mart is associated with a web service. The web service provides standard features supported by each topic focused data mart. Such standard features may include security and request/reply interactions. In addition, the web service provides custom features specific to a topic associated with each topic focused data mart. As noted above, the use of web services calls to access each topic focused data mart further enables a wide variety of connection points, in various embodiments, to the EHR, PHR, administrative dashboard, or any application designed to support a variety of calls.

In one embodiment, a request is received for at least a portion of the health data. For example, a clinician may have a patient that is eligible for certain clinical trials. The clinician may request data from a topic focused data mart that includes such information populated from at least a portion of the health data received from multiple sources.

In one embodiment, a listener is provided for updating at least a portion of the health data. As noted above, the listener allows each topic focused data mart to maintain current data. Querying the larger, public data warehouse would require significant overhead and is not a practical solution for support real-time access. However, because each topic focused data mart is streamlined with data relevant to the given topic, the listener enables each topic focused data mart to maintain up-to date data while also supporting real-time access.

In one embodiment, reporting of events identified above upper limit of normal (ULN) thresholds that occur within and/or across facilities is enabled. For example, a clinician may prescribe a certain medication to a patient. If the medication level is above an optimal threshold that is associated with an increased risk of adverse events, the medication level is identified as above ULN. The prescribing clinician may then adjust the medication level as appropriate. In another embodiment, the effect of interventions developed to reduce occurrence of the events identified above the ULN thresholds is monitored.

In another embodiment, reporting of events identified below lower limit of normal (LLN) thresholds that occur within and/or across facilities is enabled. For example, if the clinician prescribed a certain medication to a patient that is below an optimal threshold to achieve the desired benefits associated with that medication, the medication level is identified as below LLN. The prescribing clinician may then adjust the medication level as appropriate. Such reporting promotes appropriate and consistent drug monitoring to improve health outcomes. In another embodiment, the effect of interventions developed to reduce occurrence of the events identified below the LLN thresholds is monitored.

In one embodiment, the health data is associated with one or more of lifestyles, clinical trials, environmental pollution, county inspections, drug/device recalls, types of prescriptions other clinicians prescribe, most common doses, medications, and outcomes.

In practice, a web service queries a topic focused data mart to identify laboratory results flagged above ULN for inpatients that have been admitted more than 48 hours. The flagged laboratory results are used to create TDM data reports that describe the percentage of ULN events at a single facility over a 12-month period and relative to aggregate national results. Participating facilities can access the TDM data reports to support benchmarking and quality improvement initiatives.

In another example, a clinical pharmacy coordinator is responsible for coordinating pharmacy services to ensure that the pharmacy provides optimal clinical services. Upon noticing a high occurrence of ULN events at the facility, the clinical pharmacy coordinator develops quality improvement programs (i.e., interventions) to address the findings. The TDM reports are used to monitor the effect of the interventions over time and modify the programs accordingly. As can be appreciated, the TDM reports, and the overall web service, can reduce hospital safety events and improve health outcomes. In various embodiments, carbamazepine, digoxin, phenytoin, gentamicin, tobramycin, vancomycin, lidocaine, lithium, valproic acid, methotrexate levels are monitored. In other embodiments, antibiotics levels and ambulatory care specifics are monitored.

With reference to FIG. 4, an exemplary flow diagram representative of a method for presenting context-specific data derived from one or more web-accessible, topic focused data marts, in accordance with an embodiment of the present invention is shown and referenced generally by numeral 400. Method 400 may be implemented using the above-described exemplary computing system environment (FIG. 1). Initially, as shown at step 410, health data is received from at least one data source. As described above, in various embodiments, the health data is average birth weights, a list of clinical trials, comparison metrics such as length of stay by condition, TDM levels, and air quality results. In one embodiment, the health data is internal data collected by a health care facility or institution. In other embodiments, the health data is stored in large publically available data warehouses, such as statehealthfacts.org, data.gov, and clinical trials.gov. In other embodiments, the health data is stored in proprietary data warehouses. At step 420, a topic focused data mart, having at least a portion of the data received from the at least one data source is populated.

The topic focused data mart, at step 430, is associated with a web service. The web service provides standard features supported by each topic focused data mart. Such standard features may include security and request/reply interactions. In addition, the web service provides custom features specific to a topic associated with each topic focused data mart. As noted above, the use of web services calls to access each topic focused data mart further enables a wide variety of connection points, in various embodiments, to the EHR, PHR, administrative dashboard, or any application designed to support a variety of calls.

Demographic information is received from a clinician at step 440. The demographic information may include geographical information, institution information, information related to characteristics of the patient, and the like.

The clinician is presented, at step 450, with context-specific data derived from the topic focused data mart and based on the demographic information. In one embodiment, the context-specific data is average birth weights for the county, state, and/or country. In one embodiment, the context-specific data is a list of clinical trials for which a patient is eligible. In one embodiment, the context-specific data is length of stay by condition. In one embodiment, the context-specific data is TDM levels in serum across institutions. In one embodiment, the context-specific data is environmental information. In one embodiment, the context-specific data is epidemic information.

In one embodiment, a decision support engine is enabled to send alerts associated with the context-specific data. In one embodiment, the alerts provide the clinician with a warning that a certain threshold has been exceeded. In another embodiment, the alerts provide additional information associated with a patient. In another embodiment, the alerts provide the clinician with information associated with the treatment of a patient. In another embodiment, the alerts provide the clinician with information associated with clinical trial for which a patient is eligible. In another embodiment, the alerts provide a patient with information. In one embodiment, the alerts provide information related to a public health situation, such as a disease outbreak or environmental conditions.

In one embodiment, an EMR associated with a patient is automatically populated with the context-specific data. This allows a clinician treating a patient to view information associated with the health data that is relevant to the patient, without requiring the clinician to query the topic focused data mart or enter any demographic information. Rather, the demographic information is pulled from the EMR and is used to query the topic focused data mart and the context-specific data is automatically received by and presented in the EMR.

As can be understood, the present invention provides systems, methods, and user interfaces for associating multiple data sources into a web-accessible framework. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. Computer hardware storage media having computer-executable instructions embodied thereon, that when executed, perform a method for associating multiple data sources into a framework, the method comprising:

receiving health data from multiple data sources, including internal health data provided by a health care facility and publically-available health data provided by a public agency;

populating the framework comprising at least one topic focused data mart, the at least one topic focused data mart only comprising data relevant to a predetermined topic associated with the at least one topic focused data mart, the at least one topic focused data mart having a first portion of the received health data from the multiple data sources, the first portion of the received health data being associated with the predetermined topic, and the at least one topic focused data mart having a common structure;

associating the at least one topic focused data mart with a web service providing standard features supported by the at least one topic focused data mart and custom features specific to the predetermined topic associated with the at least one topic focused data mart;

receiving demographic information from an Electronic Health Record (EHR) associated with a patient;

querying the at least one topic focused data mart based on the demographic information received from the EHR to obtain context-specific data, the querying the at least one topic focused data mart comprising querying only the portion of the health data included in the at least one topic focused data mart; and presenting the context-specific data in the EHR, the receiving, querying, and presenting being performed without input from a clinician.

2. The media of claim 1, further comprising receiving a request for at least a second portion of the health data.

3. The media of claim 1, further comprising:
enabling connection points between the at least one topic focused data mart and a Public Health Record (PHR);
automatically receiving, through the connection points, demographic information from the PHR;
automatically querying the at the at least one topic focused data mart based on the demographic information from the PHR;
automatically presenting, in the PHR, context-specific data derived from the at least one topic focused data mart, the context-specific data based on the demographic information.

4. The media of claim 1, further comprising providing a listener for updating at least a third portion of the health data.

5. The media of claim 2, further comprising enabling reporting of events identified above upper limit of normal (ULN) thresholds that occur within or across facilities.

6. The media of claim 2, further comprising enabling reporting of events identified below lower limit of normal (LLN) thresholds that occur within or across facilities.

7. The media of claim 5, further comprising monitoring an effect of interventions developed to reduce occurrence of the events identified above the ULN thresholds.

8. The media of claim 6, further comprising monitoring an effect of interventions developed to reduce occurrence of the events identified below the LLN thresholds.

9. The media of claim 1, wherein the health data is associated with one or more of lifestyles, clinical trials, environmental pollution, county inspections, drug/device recalls, types of prescriptions other clinicians prescribe, most common doses, medications, and outcomes.

10. Computer hardware storage media having computer-executable instructions embodied thereon, that when executed, perform a method for presenting a web-accessible topic focused data mart, the method comprising:
receiving health data from a data source comprising at least one of receiving internal health data collected by a health care facility and receiving public health data provided by a public agency;
populating a topic focused data mart having at least a portion of the health data received from the data source, the topic focused data mart only comprising data relevant to a predetermined topic associated with the one topic focused data mart, the at least the portion of the health data being associated with the predetermined topic;
associating the topic focused data mart with a web service;
receiving demographic information from an Electronic Health Record (EHR) associated with a patient;
querying the topic focused data mart based on the demographic information received from the EHR, the querying the topic focused data mart comprising querying only the at least the portion of the health data included in the topic focused data mart; and presenting context-specific data derived from the topic focused data mart in the EHR, the context-specific data being based on the demographic information, the receiving, querying, and presenting being performed without input from a clinician.

11. The media of claim 10, wherein the context-specific data is average birth weights for a county, state, and country.

12. The media of claim 10, wherein the context-specific data is a list of clinical trials for which a patient is eligible.

13. The media of claim 10, wherein the context-specific data is length of stay by condition.

14. The media of claim 10, wherein the context-specific data is therapeutic drug monitoring levels in serum across institutions.

15. The media of claim 10, wherein the context-specific data is environmental information.

16. The media of claim 10, wherein the context-specific data is epidemic information.

17. The media of claim 10, further comprising enabling a decision support engine to send alerts associated with the context-specific data.

18. The media of claim 10, wherein the presenting comprises populating the EMR with the context-specific data.

19. A computer system for associating multiple data sources into a framework, the computer system comprising a processor coupled to a computer storage medium, the computer storage medium having stored thereon a plurality of computer software components executable by the processor, the plurality of computer software components comprising:
a health data component for receiving health data from multiple sources;
a framework component for populating the framework comprising at least one topic focused data mart, each of the at least one topic focused data mart only comprising data relevant to a predetermined topic associated with the at least one topic focused data mart, each of the at least one topic focused data mart having at least a first portion of the health data received from the multiple data sources, the at least the first portion of the health data being associated with the predetermined topic, and the each of the at least one topic focused data mart having a common structure;
a web service component for associating the at least one topic focused data mart with a web service providing standard features supported by the each of the at least one topic focused data mart and custom features specific to the predetermined topic associated with the at least one topic focused data mart;
a listener component for providing a listener for updating at least a second portion of the health data;
a request component for receiving a request for at least a third portion of the health data;
a connection component for enabling connection points to at least one of an Electronic Health Record (EHR), a Public Health Record (PHR), an administrative dashboard, and any application that can communicate with the web service;
a demographic component for receiving demographic information associated with a patient from the EHR for the patient without input from a clinician;
automatically querying the at the at least one topic focused data mart based on the demographic information from the EHR for the patient without input from a clinician, the querying the at least one topic focused data mart comprising querying only the at least the first portion of the health data included in the at least one topic focused data mart; and a presentation component for presenting context-specific data derived from the at least one topic focused data mart in the EHR for the patient without input from a clinician, the context-specific data based on the demographic information.

20. The system of claim 19, further comprising a decision support engine component for enabling a decision support engine to send alerts associated with the context-specific data.

* * * * *